United States Patent [19]
Coley et al.

[11] Patent Number: 5,657,762
[45] Date of Patent: Aug. 19, 1997

[54] METHOD FOR MONITORING OVULATION

[75] Inventors: John Coley, Northants; Paul James Davis; Philip Porter, both of Bedfordshire, all of England

[73] Assignee: Unilever Patent Holdings B.V., Rotterdam, Netherlands

[21] Appl. No.: 585,067

[22] PCT Filed: Feb. 16, 1990

[86] PCT No.: PCT/GB90/00255

§ 371 Date: Dec. 17, 1990

§ 102(e) Date: Dec. 17, 1990

[87] PCT Pub. No.: WO90/09148

PCT Pub. Date: Aug. 23, 1990

[30] Foreign Application Priority Data

Feb. 17, 1989 [GB] United Kingdom ............ 8903626

[51] Int. Cl.[6] .................................................. A61B 10/00
[52] U.S. Cl. ........................ 128/736; 128/738; 128/760
[58] Field of Search .............................. 128/738, 736, 128/778, 760; 364/413.01, 413.02, 413.03, 413.12

[56] References Cited

U.S. PATENT DOCUMENTS

| 4,408,905 | 10/1983 | Ehrenkranz | 374/157 |
|---|---|---|---|
| 4,465,077 | 8/1984 | Schneider | 128/738 |
| 4,466,445 | 8/1984 | Abrams | 128/736 |
| 4,475,158 | 10/1984 | Elias | 364/413 |
| 4,498,481 | 2/1985 | Lemke | 128/734 |
| 4,670,401 | 6/1987 | Cutler et al. | 436/65 |
| 4,676,254 | 6/1987 | Frohn | 128/736 |

FOREIGN PATENT DOCUMENTS

| 0225054 | 6/1987 | European Pat. Off. | |
| 8806863 | 9/1988 | WIPO | 128/738 |

*Primary Examiner*—Guy V. Tucker
*Attorney, Agent, or Firm*—Cushman Darby & Cushman IP Group Pillsbury Madison & Sutro LLP

[57] ABSTRACT

A method of monitoring the ovulation cycle of a female mammal, involving regular measurement of basal body temperature throughout a current ovulation cycle and occasional measurement of the level of at least one urinary component of significance in the cycle, the measurement of the urinary component being conducted at predetermined stages in the cycle to check that the level is consistent with a predicted level and thus confirm that the cycle as a whole is consistent with a prediction.

16 Claims, 8 Drawing Sheets

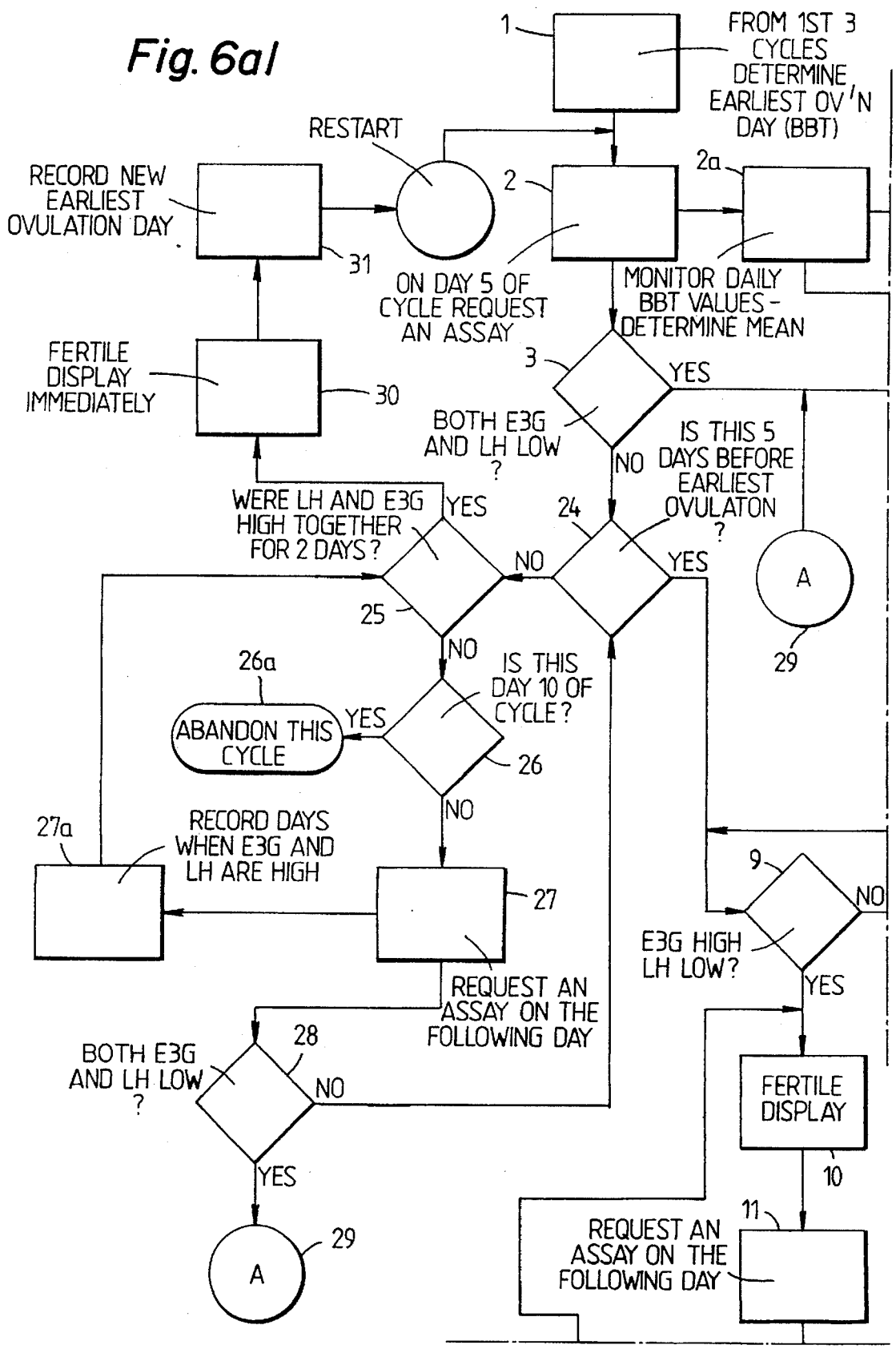
Fig. 6a1

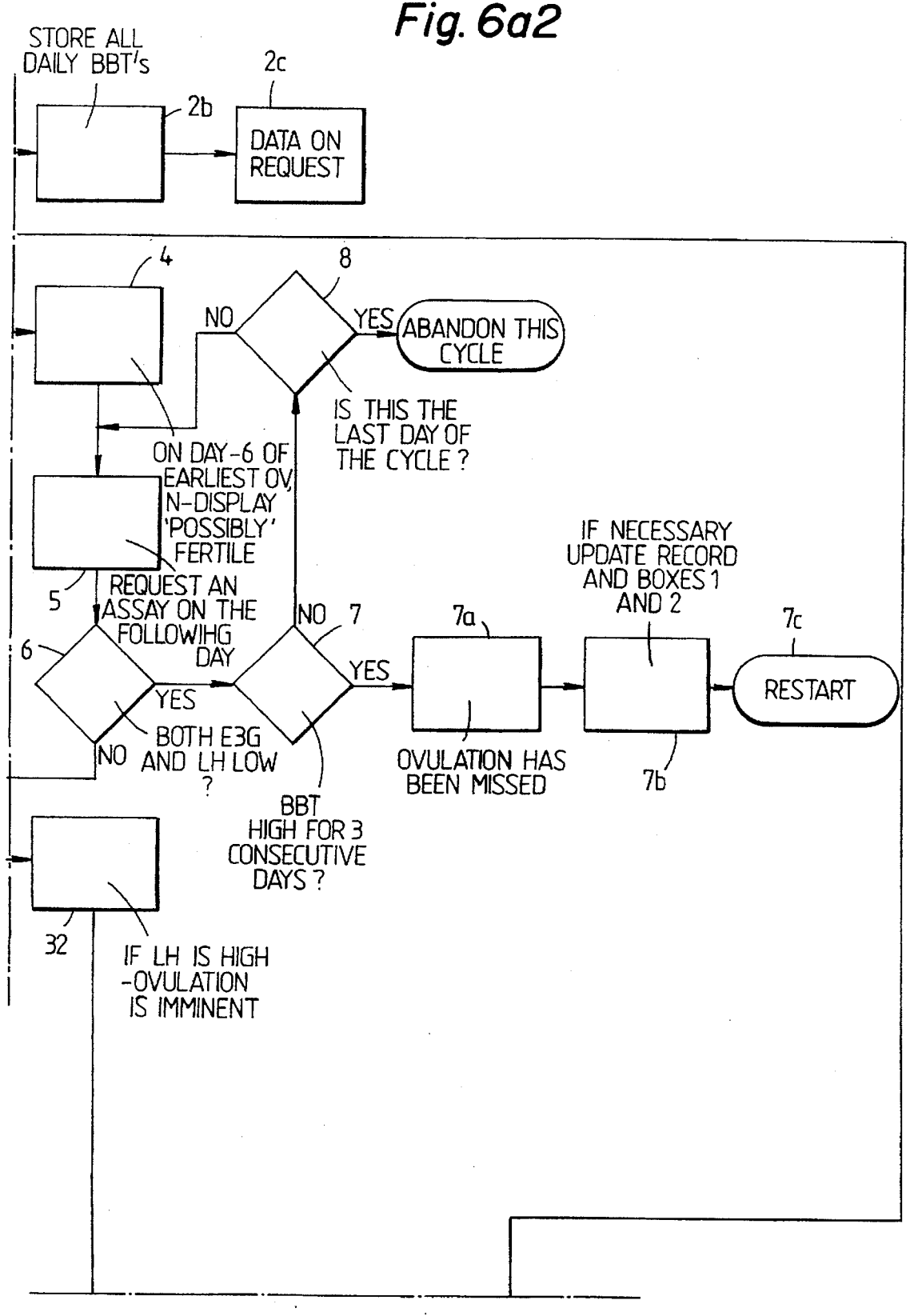
Fig. 6a2

METHOD FOR MONITORING OVULATION

CROSS REFERENCE TO RELATED APPLICATIONS

This is a 35 U.S.C. application based on PCT/GB90/00255, filed on Feb. 16, 1990.

BACKGROUND OF THE INVENTION

The present invention relates to methods and devices for use in the monitoring of the ovulation cycle in female mammals, especially humans.

Many monitoring methods have been proposed, based on a wide variety of physical or chemical bodily changes believed to be indicative of the progress of the ovulation cycle. Examples are to be found in:

U.S. Pat. No. 3,749,089 which describes an instrument for monitoring ovulation including a dual electrode vaginal probe and monitoring device, for indicating the magnitude and polarity of the electriochemical response of vaginal fluids.

U.S. Pat. No. 3,924,609 which describes a test procedure and apparatus for determining low DC potentials for measurement and identification of the different phases as well as the fact of ovulation in adult mammalian females.

U.S. Pat. No. 3,926,037, U.S. Pat. No. 3,928,423, U.S. Pat. No. 4,002,056, U.S. Pat. No. 4,013,066 and U.S. Pat. No. 4,059,986, which describe devices for determining the properties (particularly surface tension) of bodily mucus as an indication of menstrual cycle phase.

U.S. Pat. No. 3,986,494 and U.S. Pat. No. 4,010,738, which describe a method of monitoring the concentration of volatile organic compounds having a molecular weight of between 50 and 350, found in vaginal secretions.

U.S. Pat. No. 4,031,365 describes a system for continuously monitoring and displaying temperature to indicate ovulation activity.

U.S. Pat. No. 4,036,212 describes a method of monitoring the progress of the ovulation cycle which comprises periodically determining the concentration of ATP in vaginal fluid.

U.S. Pat. No. 4,119,089 describes a method for predicting and ascertaining the time of ovulation by monitoring the level of at least one volatile sulphur compound commonly occurring in mouth air.

U.S. Pat. No. 4,148,304 describes a system for determining the time of ovulation in females including a probe which measures body temperature and a probe which measures body potential together with an electronic amplification circuit and indicating device which is capable of measuring small changes in temperature and body potential and providing a portable and convenient device for determining time of ovulation.

U.S. Pat. No. 4,151,831 describes a fertility indicator for measuring and detecting the body temperature of a human subject over a menstrual cycle, having a timer for generating time based signals, and a logic circuit connected to the clock timer and being responsible to the time based signals for selecting the proper combinations of the time based signals and for indicating the correct present time. There is a temperature sensor coupled to the logic circuit for measuring the body temperature of the human subject. A solid state memory circuit having coded information command signals is coupled to the logic circuit for sequencing the logic circuit to take a plurality of temperature readings at a preset real time and to terminate the readings when the temperature has stabilized. A data storage circuit is provided for sequentially recording each of the stabilized temperatures that were measured, and a display circuit responsive to the solid state memory and data storage circuits, indicates the status of fertility of the subject during a menstrual cycle. There is also an alarm circuit coupled to the logic circuit and it has a variable pitch responsive to the solid state memory circuit for indicating the time when the subject's temperature has to be taken. Lights or words can indicate the user's status.

U.S. Pat. No. 4,151,833 describes a method for detecting ovulation by measuring the water content of the cervical mucus using a pellet made from a water-swellable polymer.

DE 2803152 describes a pregnancy preventing system using an instrument incorporating a tape cassette for recording data, a micro processor, a digital clock, an electrical temperature recorder, an acoustic signalling device, and indicator lamps.

EP 11594 describes a "pocket calculator" for forecasting menstrual cycle, using regularly entered data to predict the probability of conception.

DE 2847397 describes a microprocessor family planning calculator programmed to evaluate safe period of birth control and designed to be coupled to an existing electronic device, such as a digital alarm clock. The device includes input keys to allow data and time to be entered and an additional key to be operated at the commencement of menstruation.

U.S. Pat. No. 4,246,907 describes a method for predicting ovulation based on measuring every day throughout at least a substantial portion of the days of the menstrual cycle, the polarity of a direct current potential between at least two spaced apart portions of a woman's body.

U.S. Pat. No. 4,465,077 describes a fertility computer having the ability to store information about a user's past menstrual cycle history, basal body temperature, and gynaecological disorders which, along with certain prediction indicators, is used to predict statistically when ovulation will occur. The information is processed in accordance with a pre-determined program which ascribes certain values to the parameters to predict the present fertility status of the user.

There is at least one ovulation prediction device available commercially at present for home use which relies on the measurement of basal body temperature (BBT) and incorporates a micro-processor which adapts its prediction of the current cycle in accordance with measurements taken during preceding cycles.

Of the various methods set forth above, those utilizing the regular measurement of BBT are probably the most logical and accurate. Nevertheless, the use of BBT measurement alone is insufficiently reliable to provide an indication of the cycle status which is sufficiently accurate for contraceptive purposes. The proposal in U.S. Pat. No. 4,465,077, which combines temperature measurement with other indicators, may represent an improvement, but the additional indicator used (vaginal mucus change) is not a parameter that we believe is sufficiently significant or reliable.

Furthermore, a drawback of methods which rely primarily on the change in BBT to estimate the time of ovulation is that they are only really good at predicting the second infertile phase of a cycle occurring after ovulation (luteal phase), since the rise in BBT that occurs after ovulation can only be used to identify ovulation after it has occurred. In the absence of another reliable indicator, the first infertile phase of a cycle can only be estimated using a calendar, and a knowledge of BBT and other factors from previous cycles.

In this event, it must be falsely assumed that ovulation does not occur either earlier or later than estimated. Should ovulation occur earlier than estimated, the fertile part of the cycle will commence earlier than estimated. Should ovulation occur later than estimated, then the rise in BBT that occurs after ovulation and can be used to predict the luteal phase will not occur until later than estimated; therefore, the fertile part of the cycle will have been erroneous estimated as having started earlier than it actually did, and therefore is estimated as being unduly long.

SUMMARY OF THE INVENTION

In the light of this, there remains a need for a sophisticated detection/monitoring system, which can provide an accurate indication of the ovulation cycle status based on parameters which are scientifically credible and reliable, and which enables a predicted cycle (based on measurements from previous cycles) to be verified easily.

It is already known that significant changes in the levels of certain urinary hormones occur during the ovulation cycle. For example, ovulation prediction devices which measure the level of LH hormone in urine are available commercially for home use. Such devices are a useful aid to conception, but do not alone provide a long enough "warning" of likely ovulation to be reliable for contraceptive purposes.

No attempt has previously been made to link the measurement of such hormones with other factors (particularly BBT) to provide a composite system for monitoring and predicting ovulation.

The present invention provides a method of monitoring the ovulation cycle of a female mammal, of particular use with humans, involving measurement of BBT (basal body temperature) and occasional measurement of the level of at least one urine component of significance in the cycle. Preferably, the measurement of BBT is conducted on a frequent, regular basis, e.g. daily, at least during an initial series of cycles, to establish an outline precise record of the typical cycle of the individual being monitored. The measurement of the urine component is preferably conducted at a predetermined stage in the cycle to check that the level is consistent with a predicted level, and thus confirm that the cycle as a whole is consistent with a prediction. By linking regular, eg. daily, measurement of BBT to an occasional measurement of at least one relevant urine component, such as a hormone that can be detected by an easily performed immunoassay test, much improved reliability in the monitoring of the cycle can be achieved. Daily measurement of the urine component throughout the cycle is, however, unnecessary.

Preferably, the measured BBT is recorded on a microprocessor programmed to predict the progress of the cycle in terms of expected BBT and also in terms of the expected level of the urine component, and to provide an indication to the user of the current stage in the cycle. Preferably, the micro-processor is programmed to provide the user with an indication that the level of the urine component should be measured. Preferably, the micro-processor can modify (if necessary) its prediction of the present cycle, or of a future cycle, on the basis of actual measurements recorded.

Even greater reliability can be achieved if the levels of at least two urine components are measured. Appropriate Urine components are E3G, (estrone-3-glucuronide) P3G (progesterone-3-glucuronide) and LH (lutenizing homone). Of these, LH is the most useful. Preferably the levels of at least two urine components are measured simultaneously, e.g. E3G and LH. Conveniently, the level of urinary E3G is measured on at least one day during the interval from day 5 to 7 of the predicted cycle, and again on at least one day during the interval from day 10 to day 15 of the predicted cycle. Conveniently, the level of urinary LH is measured on at least one day during the interval from day 13 to day 16 of the predicted cycle.

Conveniently, the level of the urinary component being measured is measured on at least 2 successive, or at least closely spaced days in the predicted cycle to determine whether the level is constant, increasing or declining.

If the level of a urine component does not conform to a predicted level when tested, e.g. through natural fluctuation and variability of urine volume, the test should be repeated on subsequent successive or at least closely spaced days in the predicted cycle to check the situation.

The invention also provides a device for monitoring the ovulation cycle of a female mammal, comprising means for initiating the recording of a cycle, means for measuring BBT, means for recording the measured BBT, if necessary throughout the cycle, means for predicting the cycle on the basis of the measured BBT, means for predicting the level of at least one urine component at a predetermined stage in the predicted cycle, means for responding to a measured actual level of the urine component when the predetermined stage is reached, and means for indicating to a user of the device the current stage of the cycle and/or the state of fertility of the individual being monitored.

Preferably, the device incorporates means to indicate to the user that the level of urine component should be measured and recorded.

Information can be conveyed to the user by means of a liquid crystal or LED display, for example. If desired, information on the state of fertility can be conveyed by a simple visual indication, e.g. a combination of colours showing, for example, green for infertile, red for fertile, and yellow for any intermediate stage when conception is less likely but still possible. Especially if the device is intended primarily as an aid to contraception, it should "fail safe" by showing a "fertile" signal.

Preferably, the device has been programmed to modify (if necessary) its prediction of the present cycle, or of a future cycle, on the basis of actual measurements recorded during one or more previous cycles.

The invention further provides a kit for monitoring the ovulation cycle of a female mammal, comprising a monitoring device as set forth above, together with at least one testing device capable of being used to measure the level of one or more urine components. It is envisaged that the monitoring device will generally be of a relatively durable nature and capable of being used over a considerable number of cycles. The testing devices for measuring the urine components are preferably disposable after individual use, and it is therefore envisaged that the user of the monitoring device will need to replenish the testing devices.

BBT can be measured using, for example, a thermometer giving a visible readout, or a probe connected directly to an electronic timer or micro-processor. In the former situation, it will be necessary for the user to relay the temperature information to the timer/micro-processor eg. by entering the temperature via a key pad built into the timer/microprocessor. Temperature sensitive probes linked directly to timers/micro-processors are described, for example, in U.S. Pat. No. 4,465,077.

Measurement of the urine component must be done on a urine sample. A variety of immunoassay techniques are available which enable such urine components to be measured. A wide variety of solid phase testing devices such as dipsticks and chromatographic strips have been described in the literature, and can readily be adapted for use in determining urinary hormones. In the present context, it is not envisaged that such an assay would need to be quantitative, but rather a "yes/no" answer will be sufficient provided that the distinction between a positive and a negative test result is pitched at a suitable threshold concentration. Of course, if the hormone test produces a gradation of results, eg. of a "low/intermediate/high" nature, this will enable the resulting monitoring process to be even more accurate. Examples of simple assay technology that can readily be adapted for use in the home is described, for example, in EP 0225054, EP 0183442, EP 0186799 and GB 2204398. Disposable assay strips such as those described in GB 2205398 which simply require to be contacted with urine and which provide an assay result in semi-qualitative form (eg. by means of a series of test zones on the strip which are progressively positive at higher urinary hormone levels) can be used.

In a more sophisticated version of an apparatus according to the invention, the timer/microprocessor can incorporate means for reading the result of the urine assay, eg. by measuring the reflectance or fluorescence from an assay strip. This may enable a more precise numerical indication to be given of the urinary component level, and further enhance the accuracy of the ovulation prediction.

In an embodiment of the invention in which two or more urinary components are measured simultaneously, such measurement can if desired be performed using a single urine assay device, eg. a device incorporating multiple assay strips or a single strip capable of independently detecting the level of the different components. Multiple analyte tests are described in GB 2204398.

The detailed electronics of a timer/microprocessor capable of assimilating, remembering and handling such data, as well as providing the preferred electronic features of the device discussed herein, and predicting future cycles on the basis of such data, can readily be provided by those skilled in the electronics art once they have been advised of the factors that such a device must take into consideration, and the data that the device must provide for the user. Such detailed electronics does not form part of the invention. However, by way of example only, and as a guide to the requirements placed on such a device, an algorithm depicting a typical flow of information required in a monitoring method according to the invention is described.

BRIEF DESCRIPTION OF THE DRAWINGS

FIGS. 6a, 6b show an example of an algorithm which can be applied to data to predict the fertile period, based on measures of E3G, LH and BBT as, for example, graphically shown in FIG. 5.

DETAILED DESCRIPTION OF THE PREFERRED EMBODIMENT

By way of example only, aspects of the invention are illustrated in the accompanying drawings. These relate to the monitoring of the human ovulation cycle.

Figure 1:
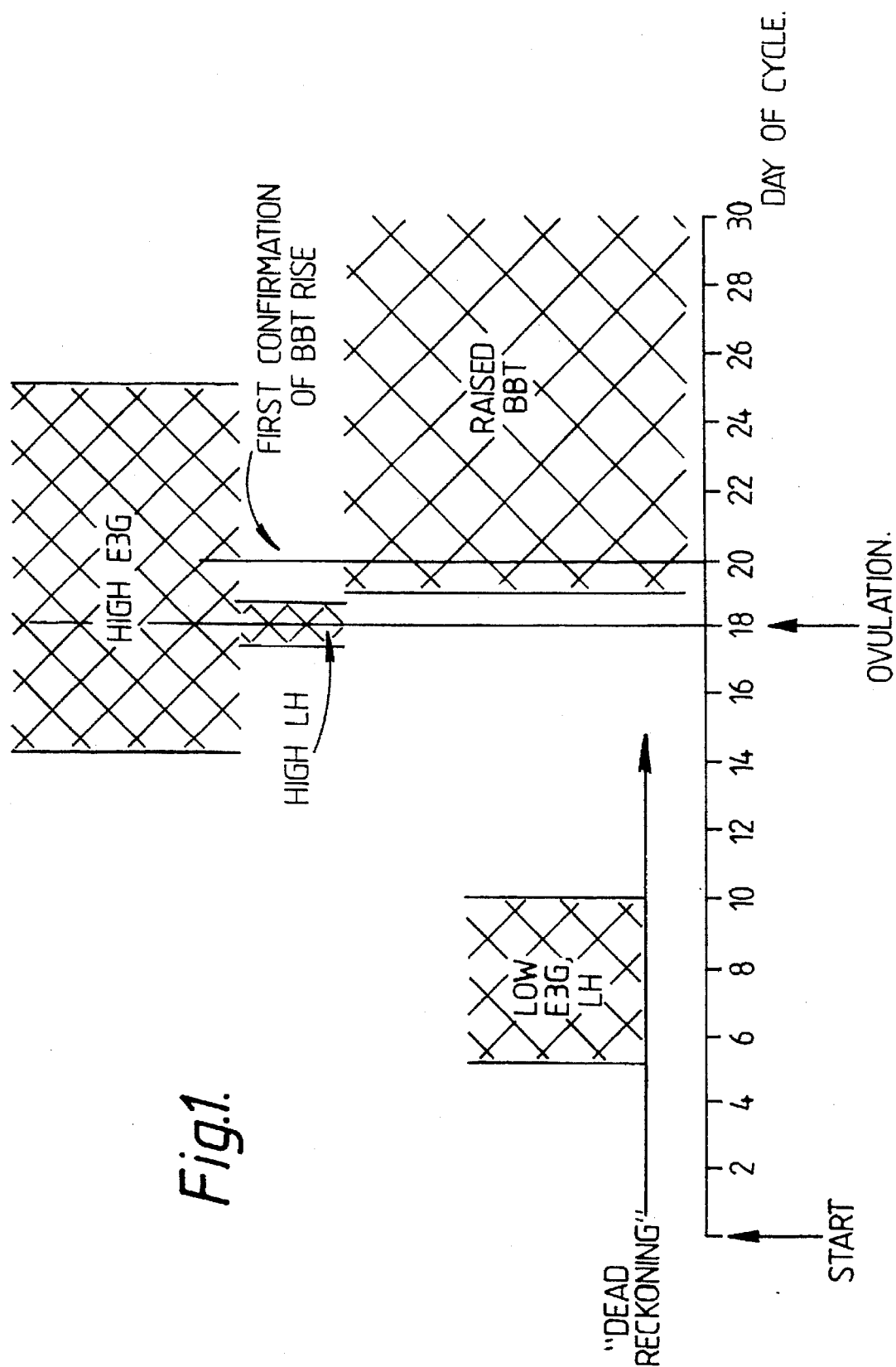
FIG. 1 illustrates the idealized changes in the levels of readily measurable markers that take place during a typical ovulation cycle.

FIG. 1 illustrates the idealized changes in the levels of readily measurable markers that take place during a typical ovulation cycle. When the method of the invention is first applied by a user, this typical cycle is used as a model and the extent to which the actual cycle conforms with or deviates from this typical cycle can be monitored as the cycle progresses. This influences predictions of subsequent cycles. The user can initiate the observations from the first day of menstruation. Daily temperature readings will be needed and the levels of the various hormones can be checked at the appropriate intervals during the cycle.

Figure 2:
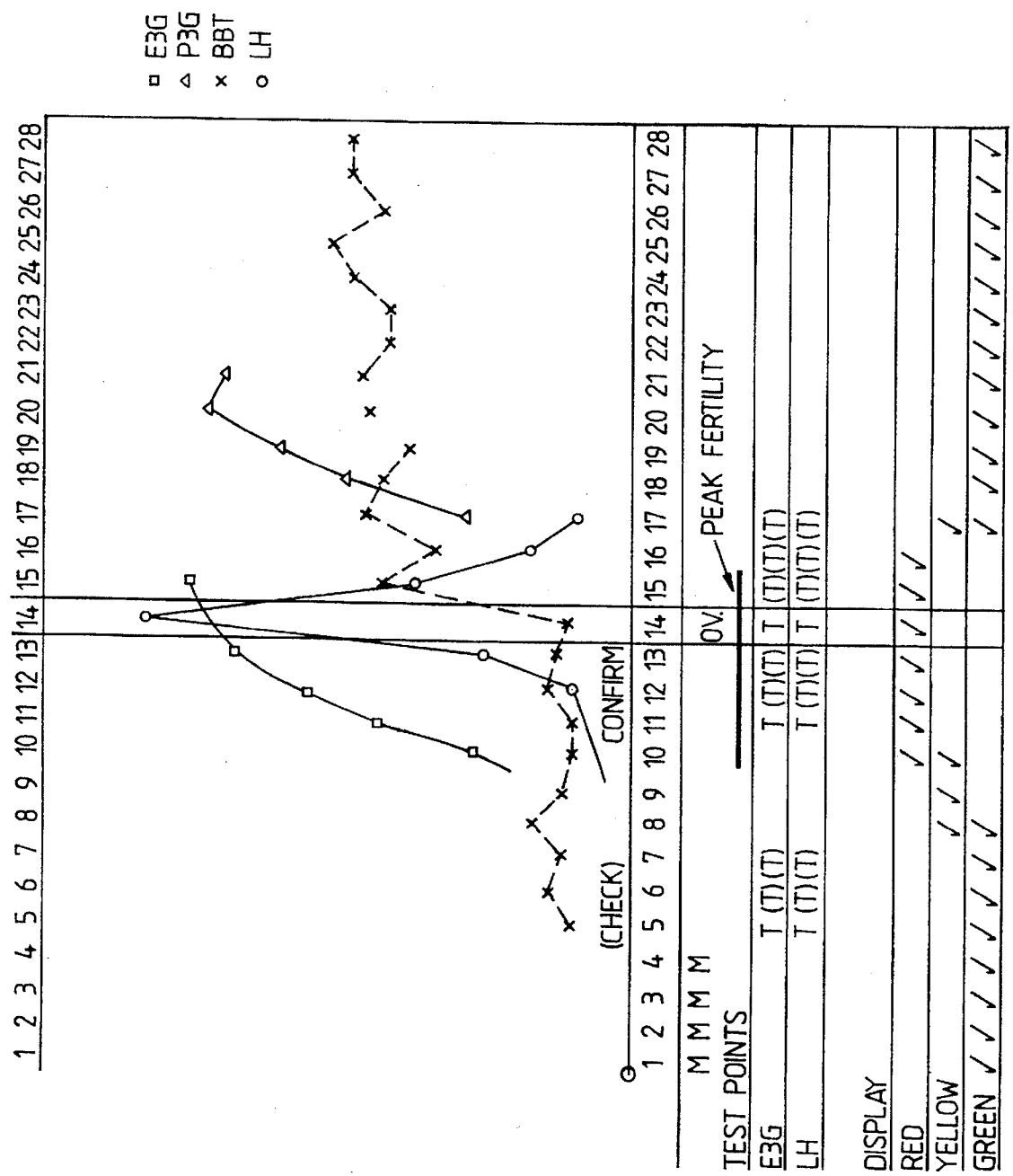
FIG. 2 is a generalized graph of the chemical testing points that may be used to determine with greater accuracy the actual progress of the cycle.

FIG. 2 is a generalized graph of the chemical testing points that may be used to determine with greater accuracy the actual progress of the cycle. These are indicated by T, and additional testing points (T) which may be required to confirm the results of the initial tests. In a successfully predicted cycle, the tests conducted over the day 5 to day 7 interval as shown in the drawing will show E3G low and LH low. The test at day 11 will show E3G high and LH low. The test at day 14, will show both E3G and LH high. Information on the state of fertility can be conveyed to the user by means of a display as represented by the red/yellow/green indicators.

Figure 3:
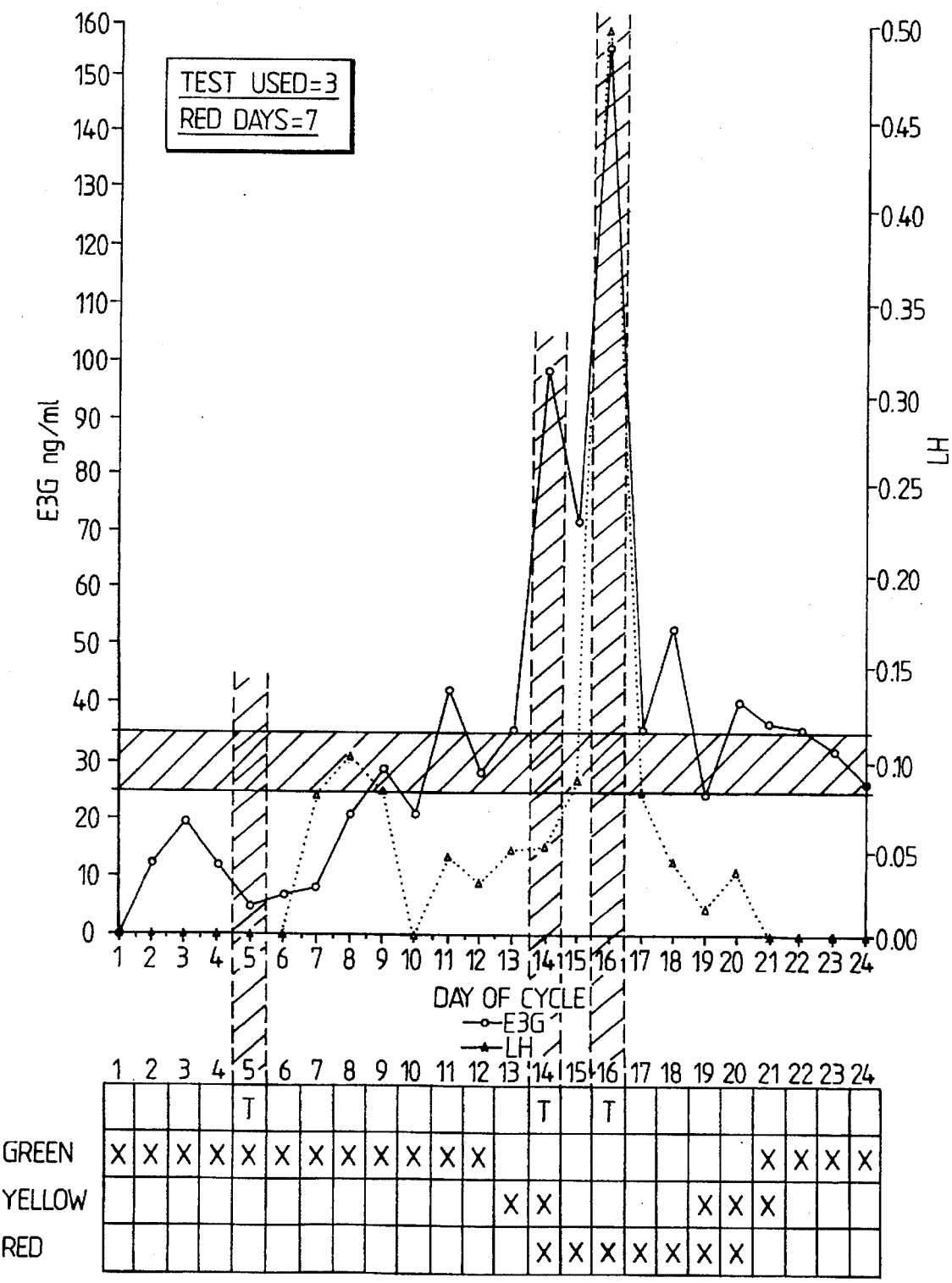
FIGS. 3 and 4 show changes in the levels of E3G and LH from urine samples collected during two different "live" cycles.
Figure 4:
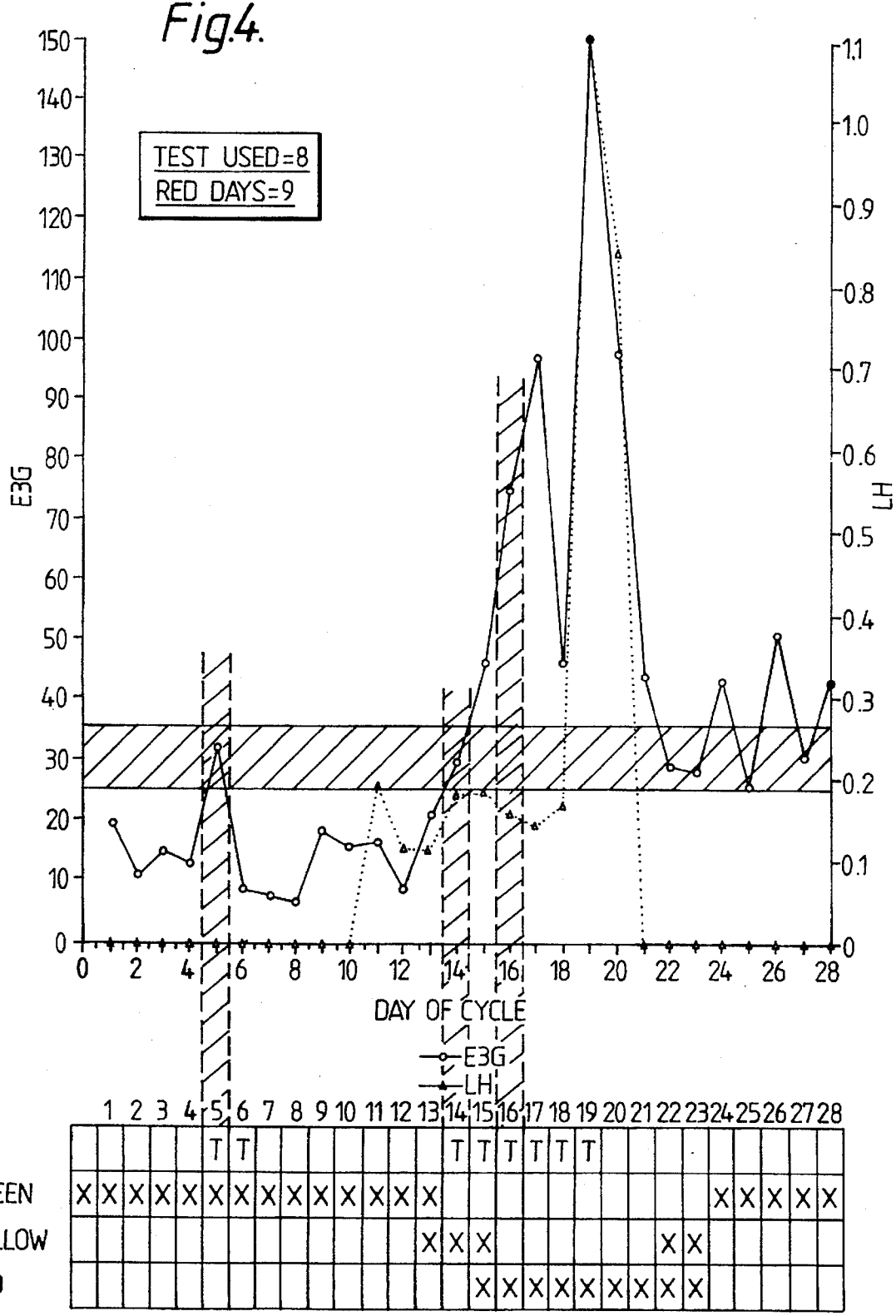

FIGS. 3 and 4 show changes in the levels of E3G and LH from urine samples collected during two different "live" cycles. The horizontal cross-hatched zone in FIGS. 3 and 4 represents a chosen demarcation and hormone levels above this zone are rated as "high" while hormone levels below this zone are rated as "low". If any test shows a hormone level within the demarcation zone, it is treated as ambiguous and therefore requires further hormone level testing on at least one subsequent day. FIGS. 3 and 4 also illustrate the considerable variation that can occur from one cycle to another in the same individual and hence the need for a monitoring method to be able to recognise such variation and to identify when additional testing is required, so that more accurate information can be displayed.

Figure 5:
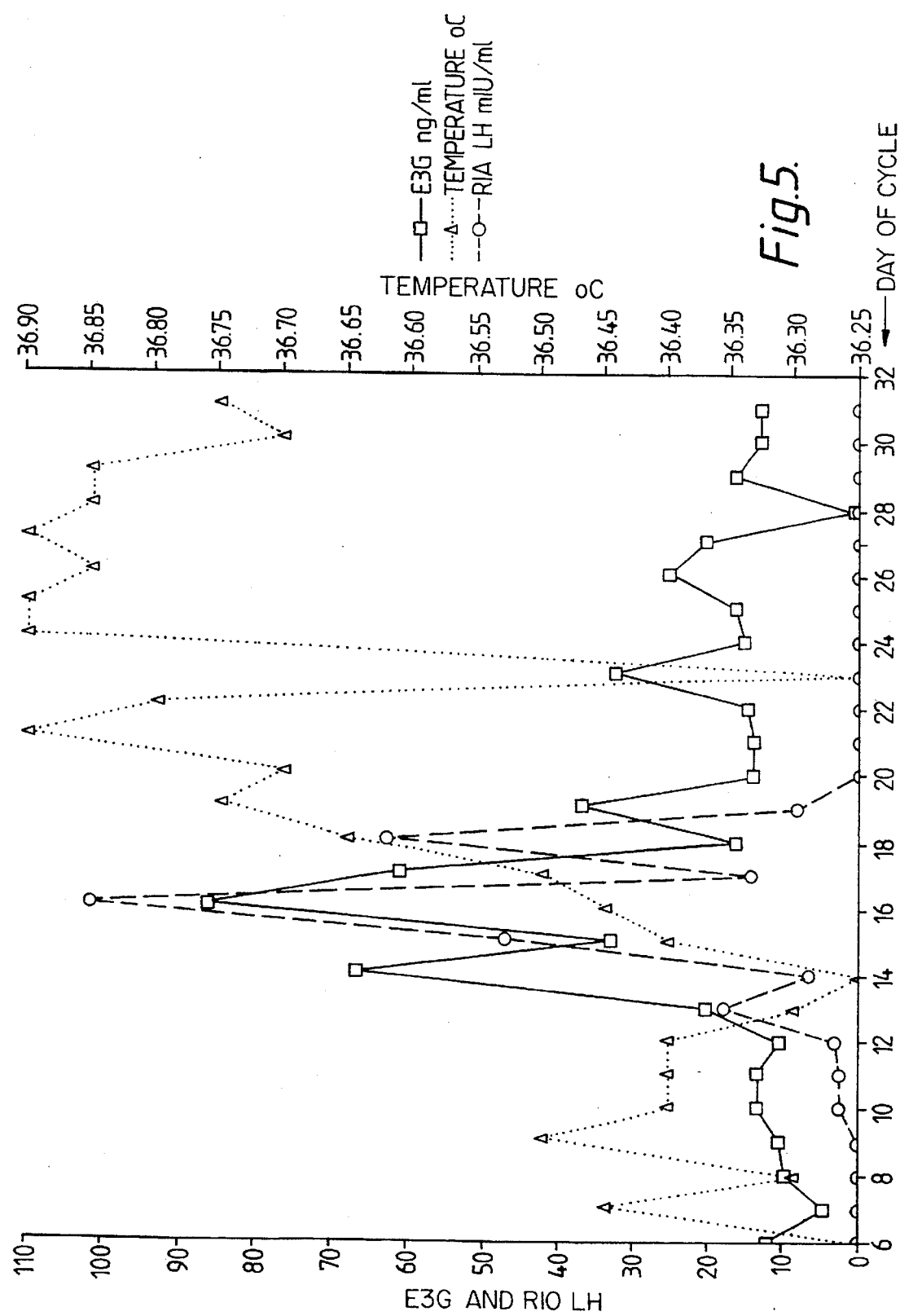
FIG. 5 shows measures of E3G concentration, LH concentration, and temperature for another typical cycle.

FIG. 5 shows measurements of E3G concentration, LH concentration, and temperature for another typical cycle. E3G measurements were obtained from a laboratory dipstick competitive enzyme immunoassay. LH measurements were obtained from a commercially available radioimmunoassay. Temperature measurements were obtained using a clinical thermometer, with the results recorded on a recording chart. The graph obtained demonstrates general trends that are normally observed in temperature and levels of E3G and LH during a menstrual cycle.

Figure 6B:
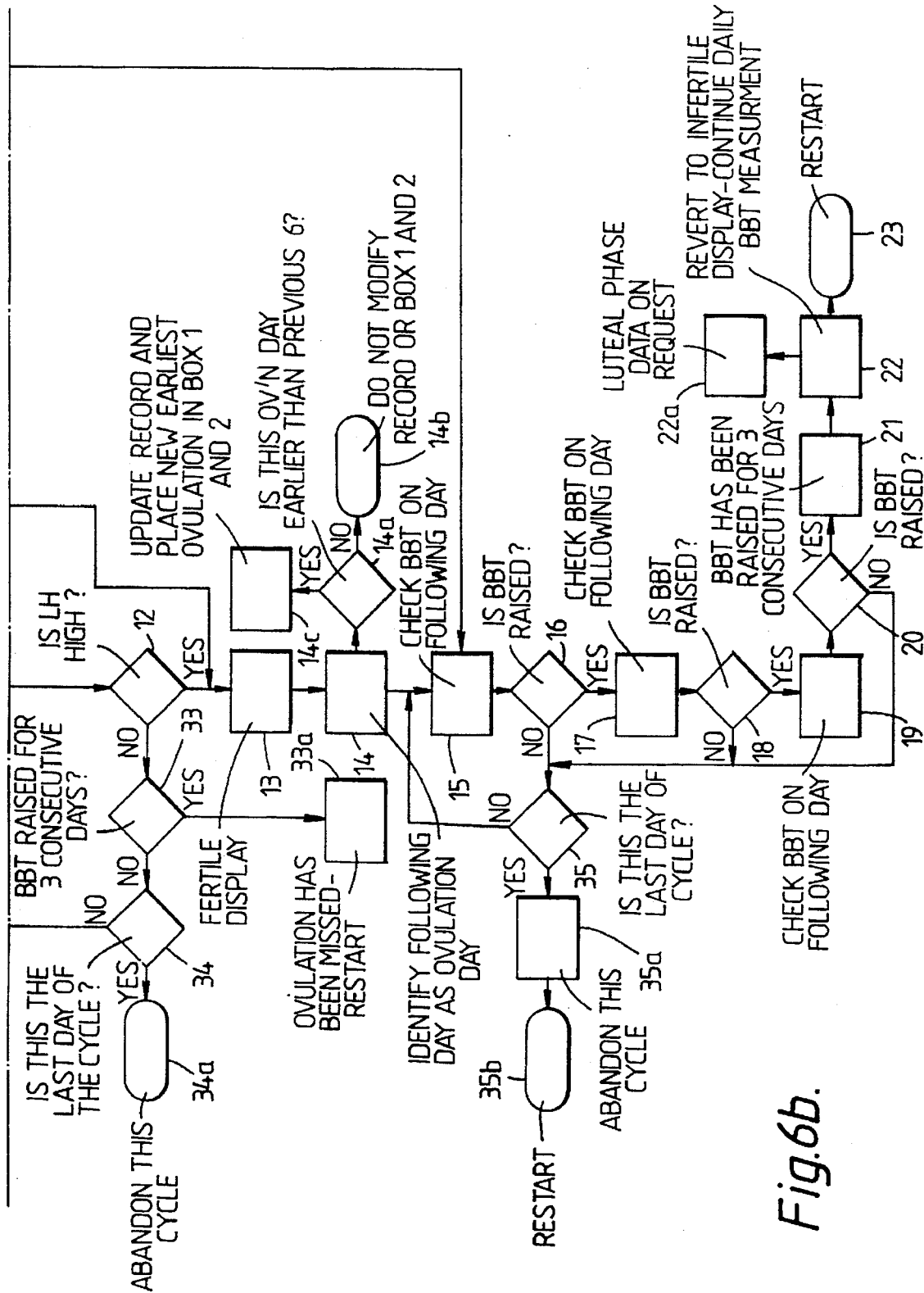

FIGS. 6a, 6b show an example of an algorithm which can be applied to data to predict the fertile period, based on measurements of E3G, LH and BBT as for example graphically shown in FIG. 5. The "assay" requested at various points in the algorithm is preferably a dual assay, capable of measuring E3G and LH simultaneously but individually. In the following discussion, which generally refers to the data shown in FIG. 5, threshold values of concentration for E3G and LH may be regarded as 40 ng/ml and 30 miliIU/ml; above these values, the concentration of the hormone may be regarded as "high". For the purposes of the algorithm, the last day of the cycle is regarded as the first day of menstrual bleeding in the next cycle.

The user initiates the process by indicating to the monitoring device that a new cycle has begun. Prior to this (as shown by box 1), it is necessary to determine the earliest expected ovulation day, predicted from data acquired from one or more previous cycles in which LH or BBT measurements have been made.

Using the data presented in FIG. 5, the algorithm can be traced as follows:

On the basis of data received from previous cycles, the monitoring device predicted that ovulation would occur at day 16 of the cycle.

An initial request for a dual assay (box 2) for urine E3G and LH is made on day 6 of the cycle. The monitoring device analyzer the results (box 3) to determine whether the levels of E3G and LH were both low. In the cycle of FIG. 5, they were both low, meaning that the "yes" route is followed to box 4. In box 4, the instruction is given that, 6 days before the earliest expected ovulation day, (day 10) a "possibly fertile" warning is displayed. Five days prior to predicted ovulation (box 5), a further assay is requested. After the assay has been completed, the monitoring device determines (box 6) whether the levels of E3G and LH were both low. They were both low, and therefore the "yes" route is taken to box 7, and the question of whether the BBT measurements, which have been taken daily from day 6 of the cycle onwards, have been high for 3 consecutive days, is asked. This is to identify whether ovulation may have occurred without a detectable rise in hormone levels.

In this case, BBT had not been high for 3 consecutive days and ovulation had not been missed, so the "no" route is followed to box 8, where a check is made to see that the end of the cycle has not been reached. As it had not, the "no" route is followed back to box 5, requesting an assay On the subsequent day. In this cycle, the loop involving boxes 5, 6, 7 and 8 is traversed 3 times, by which time on day 14 of the cycle the answer to the question in box 6 is that both E3G and LH were not low.

Consequently, the "no" route is followed from box 6 to box 9, which asks whether E3G was high and LH was low. The answer was "yes", providing warning that the fertile period has started, and the monitoring device indicates to the user a fertile status, as shown by box 10. Moving on to box 11, an assay is requested on the following day. At this point of the cycle, only the LH level need be determined, so box 12 asks whether the level of LH was high. LH was high on day 15, so the fertile display is maintained (box 13), and according to the algorithm the following day (day 16) is identified as the ovulation day (box 14).

Whilst the algorithm has identified ovulation as occuring on day 16, it is debatable whether ovulation occurs on the day following a sharp rise in the LH concentration, (ie day 16), or the day following the LH concentration peak (ie day 17). Similarly, the day following ovulation is generally regarded as first day of "high" BBT.

Box 14a is a check to see whether it is necessary to update the earliest expected ovulation day, with box 14b showing that it is not necessary to modify the record if the answer to the question of box 4a is "no", and box 14c showing the action of updating if the answer is "yes".

Continuing the normal run of events, box 15 shows that the system now reverts solely to BBT for its information, and does not require any more hormone assays to complete the analysis of this cycle, so (in box 15) BBT is checked on the following day (ovulation day). The next important signal that the monitoring device looks out for is elevated BBT over three consecutive days. BBT is elevated from day 17 onwards, so the answer to the question in box 16 is "yes", and BBT is checked on the following day (box 17). Continuing, box 18 asks whether BBT is again raised, a "yes" response leading to box 19 which checks BBT on the next day. Again it is asked (box 20) whether BBT is raised. A "yes" answer leads to box 21, where it is asked whether BBT has been raised for three consecutive days. A "yes" to this indicates that the fertile phase has ended, and that an infertile display can be shown (box 22). BBT routine measurement is continued on request (box 22a) to complete the record of data.

In box 23 the process is re-started by the user at the beginning at the next cycle.

BBT is monitored throughout the cycle, starting on day 6 (box 2a) at the same time as the first hormone test is requested. Box 2b shows that the BBT values must be stored, and the data must be accessible on request (box 2c) for use in various parts of the algorithm, and for analysis of any malfunction. The route from box 2a to box 15 provides the data by which elevated BBT may be determined, with reference to the values of BBT recorded in the first part of the cycle.

The result of the first test on day 6 (box 2) could be that E3G and/or LH are raised (a "no" response to box 3), so it is necessary to define whether this is an early ovulation occurring well before the expected ovulation time, or whether it is simply a random variation possibly caused for example by malfunction of the test, or by very high urine concentration. If either of these hormones were elevated, then the answer to the question in box 3 is "no", leading to box 24 which asks whether the day of the cycle is 5 days before the earliest prediated ovulation. If the answer is "yes", the hormone profile could be developing as normal on time through a pre-ovulatory phase. This "yes" route therefore leads to box 9, which attempts to follow the normal expected pattern of hormone variation leading up to ovulation.

If the answer from box 24 is "no" (leading to box 25), it is necessary to continue testing to find whether both LH and E3G are generally low, and the negative answer at box 3 was caused by an isolated "spike" in the level of one hormone, thereby suggesting that the cycle is behaving predictably, or whether other variations in the hormone levels are occuring for other reasons. In going around the loop involving boxes 25, 26, 27 and 27a, box 25 checks whether LH and E3G have been recorded high together for 2 consecutive days of the cycle, where the loop had been previously traversed. A "yes" answer indicates an exceptionally early ovulation, and leads to box 30, where a fertile display is given immediately. At box 31 the new earliest ovulation day is recorded for future reference.

If the answer to box 25 is "no" (as it will be on the first occassion this loop is encountered), then the algorithm progresses via box 26 to box 27, at which it requests another assay. The results of this assay are fed via box 27a to box 25, where they may be needed. When the assay of box 27 is conducted, box 28 asks whether both E3G and LH levels are low. If the answer is "yes" (as would be expected for a normal cycle) the algorithm progressed to box 29, and thus to box 29a. At this point the algorithm feeds back into box 4, and resumes a normal route.

If, however, the answer to box 26 is "no", and therefore E3G and/or LH is still high, the algorithm feeds back to box 24, where it again asks whether the day reached in the cycle is 5 days before early ovulation. A "yes" answer to this leads to box 9 and normal continuation of the algarithm, whereas a negative answer feeds back into the loops involving boxes 25–26–27–27a and boxes 25–26–27–28–24.

The purpose of these loops is to try to establish a low reading for E3G and LH during the early part of the cycle (days 6–10), unless the user is experiencing early ovulation. If early ovulation does occur, the algorithm follows the route from box 24 either via boxes 25–30–31, or to box 9 and onwards depending on whether the day of early ovulation in the cycle was predicable from previous data or not. If satisfactory low values of E3G and LH cannot be established during these early days of the cycle, then these loops will continue to be traversed until box 26 is reached on day 10, at which time the algorithm will abandon predictions for this particular cycle (box 26a).

At box 7, BBT measurements are used to check whether early ovulation has been missed by hormonal measurements. If three consecutive days with elevated BBT have been recorded, it can be assumed that ovulation has occurred, so the "yes" route to box 7a would be taken, implying that ovulation has been missed by the hormonal analysis. Continuing, box 7b shows that it may be necessary to update the record for use in boxes 1 and 2. After this, no further action is required until the next cycle.

It is expected at box 6 that E3G and LH should both be low for around 3 days after request for assay, but if they are not, the "no" route is followed, leading to box 9 where it is asked whether E3G is high and LH low. If the answer is "no", then of course LH is high, and a high LH at this point is taken to be the most significant physiological signal that ovulation is imminent (box 32). Boxes 10 to 12 are then by-passed, leading directly to box 13 (fertile display). The following day is recorded by the monitoring device as ovulation day (box 14).

In the normal course of events, E3G should be high before LH is found to be high, giving the answer "yes" to the question of box 9. This provides a clear and timely warning signal that the fertile period is commencing, so the "yes" route from box 9 leads directly to a fertile display (box 10). Box 11 shows an assay requested on the following day, and here the algorithm is looking for a high LH value which would provide a signal for ovulation on the following day. This is shown in box 12. However, it is possible that some of the assays requested in box 11 may provide low H values, in which case the "no" route from box 12 would be followed, leading to box 33. The question asked at box 33 is whether the BBT has been raised for 3 consecutive days. This is to check that there has not been an ovulation which has been missed by the hormonal analysis. The box indicated by 33a (ie. a "yes" answer to the question of box 33) is equivalent to the sequence shown by boxes 7a, 7b and 7c. If the "no" route is followed from box 33, box 34 checks that this is not the last day of the cycle. Box 34a indicates that the analysis of the cycle would be abandoned if no high LH and no raised BBT had been found before the end of the cycle. In the normal course of events, it is expected that the answer to box 34 would be "no", so the route leads back to box 10, maintaining the fertile display which was instigated by the high E3G value found previously (box 9). This loop going from 12 to 33, 34 and back to 10, is repeated until some indication of ovulation is found (a "yes" response from box 12).

The fertile display should be switched off by finding the BBT elevated on 3 consecutive days, shown by boxes 15 to 21. The answers to the questions in boxes 16, 18 and 20 ought to be "yes" after normal ovulation, but if the temperature is not raised on consecutive days, then one or more of those questions will be answered "no". In this case, the route from any of boxes 16, 18 or 20 goes back to box 35 which checks that it is not, the last day of the cycle; if it is not the route loops back to box 15, and the BBT is checked again the following day. If it is not possible to find BBT raised on 3 consecutive days before the last day of the cycle ("yes" to box 35), then the cycle has not been successfully analyzed (box 35a). The fertile display then remains on until the end of the cycle, since box 22 is never reached (where the display would have reverted back to infertile).

We claim:

1. A method of monitoring the ovulation cycle of a female mammal to provide contraceptive advice during a current ovulation cycle, said method involving regular measurement of basal body temperature throughout said current cycle and occasional sampling of the urine to measure the concentration of at least one component of the urine of significance in said cycle, said measurement being conducted at predetermined stages in said current cycle to check that the concentration of said component is consistent with a concentration predicted on the basis of measurements made during at least one previous cycle and thus confirm that said current cycle, as a whole, is consistent with a prediction on the basis of said one previous cycle.

2. A method according to claim 1, wherein said measured basal body temperature is recorded on a micro-processor programmed to predict the process of said current cycle in terms of expected basal temperature and also in terms of an expected level of said urine component, and to provide an indication to the user of the current stage in said current cycle.

3. A method according to claim 2, wherein said microprocessor is programmed to provide said user with an indication that said level of said urinary component should be measured.

4. A method according to claim 1, wherein the levels of a plurality of urinary components are measured at different stages in the cycle.

5. A method according to claim 1 wherein E3G is said urine component and the level of E3G in the urine is measured.

6. A method according to claim 1, wherein P3G is measured.

7. A method according to claim 6, wherein said level of urinary E3G is measured on at least one day during the interval from day 5 to day 7 of said current cycle and again on at least one day during the interval from day 10 to day 15 of said current cycle.

8. A method according to claim 1 or 6, wherein the level of urinary P3G is measured on at least one day during the interval from day 17 to day 21 of the predicted cycle.

9. A method according to claim 1, wherein the level of urinary LH is measured.

10. A method according to claim 9, wherein said level of urinary LH is measured on at least one day during the interval from day 13 to day 16 of said current cycle.

11. A method according to claim 1, for use with a human.

12. A method according to claim 1, wherein basal body temperature is recorded daily.

13. A method according to claim 1, wherein the level of the urine component being measured is measured on at least 2 successive, days in said current cycle to determine whether said level is constant, increasing or declining.

14. A device for monitoring the ovulation cycle of a female mammal to provide contraceptive advice during a current ovulation cycle, comprising means for measuring basal body temperature, means for recording said measured basal body temperature throughout said current cycle, means for predicting said current cycle on the basis of said measured basal body temperature, means for predicting, on the basis of measurements made during at least one previous cycle, the concentration of at least one component in the urine at a predetermined stage in said current cycle, means for recording a measured actual level of said urine component when said predetermined stage is reached, and means, associated with said recording means, for indicating to a user of said device the current stage of said current cycle so as to determine if said current stage is consistent with a prediction based on measurements made during a previous cycle.

15. A device according to claim 14, wherein said device incorporates means to indicate to said user that said level of said urinary component should be measured and recorded.

16. A device according to claim 14, programmable to modify its prediction of said current cycle or a future cycle in consequence of actual measurements recorded during one or more previous cycles.

* * * * *